Figure 1:
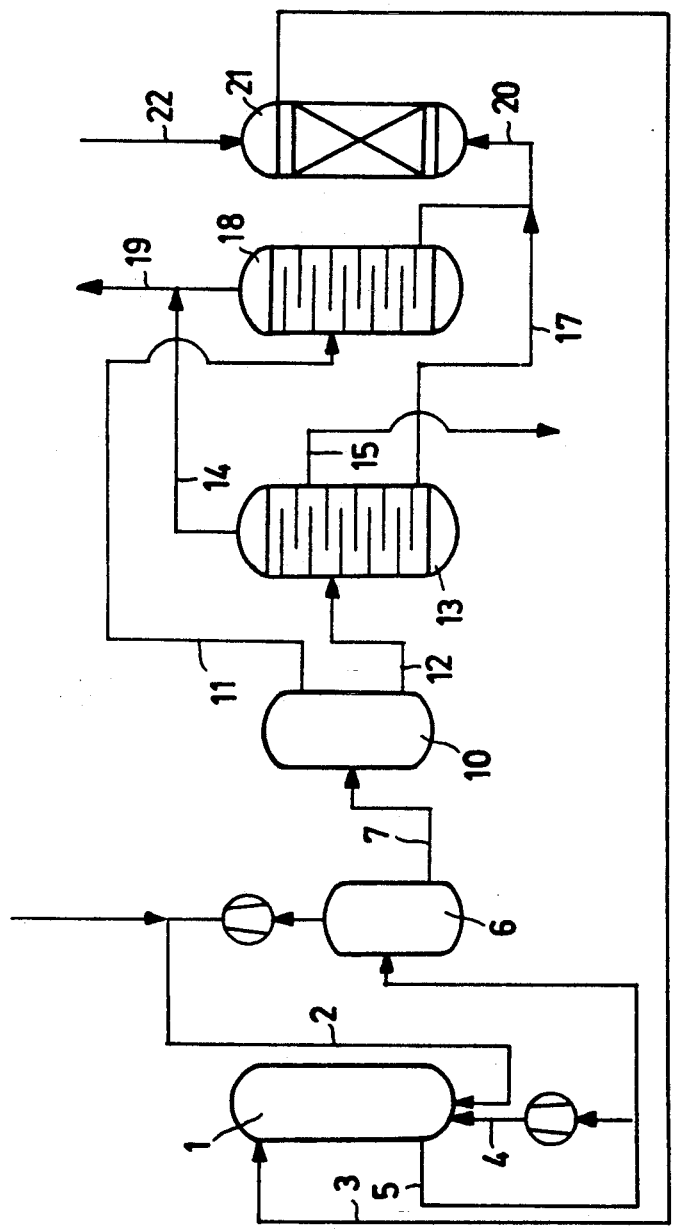

United States Patent [19]
Clerici et al.

[11] Patent Number: 5,221,795
[45] Date of Patent: Jun. 22, 1993

[54] PROCESS FOR PRODUCING OLEFIN OXIDES

[75] Inventors: Marjo G. Clerici; Patrizia Ingallina, both of San Donato Milanese, Italy

[73] Assignee: Eniricerche S.p.A., Milan, Italy

[21] Appl. No.: 923,326

[22] Filed: Jul. 31, 1992

[30] Foreign Application Priority Data

Aug. 2, 1991 [IT] Italy ............... MI91 A/002196

[51] Int. Cl.$^5$ ............... C07D 301/08; C07D 301/12; C07D 303/04
[52] U.S. Cl. ............... 549/531; 549/533
[58] Field of Search ............... 549/533, 531

[56] References Cited

U.S. PATENT DOCUMENTS

| | | | |
|---|---|---|---|
| 3,597,459 | 8/1971 | Mimoun et al. | 549/533 |
| 4,410,501 | 10/1983 | Taramasso et al. | 423/326 |
| 4,824,976 | 4/1989 | Clerici et al. | 549/531 |
| 4,833,260 | 5/1989 | Neri et al. | 549/531 |

FOREIGN PATENT DOCUMENTS

| | | | |
|---|---|---|---|
| 9262 | 4/1980 | European Pat. Off. | 549/531 |
| 0100119 | 2/1984 | European Pat. Off. | |
| 0226257 | 6/1987 | European Pat. Off. | |
| 0226258 | 6/1987 | European Pat. Off. | |
| 0266825 | 5/1988 | European Pat. Off. | |
| 315248 | 5/1989 | European Pat. Off. | 549/531 |
| 1817717 | 2/1970 | Fed. Rep. of Germany | 549/531 |
| 3205648 | 8/1983 | Fed. Rep. of Germany | |
| 1209321 | 10/1970 | United Kingdom | 549/531 |

OTHER PUBLICATIONS

Kirk–Othmer, "Encyclopedia of Chemical Technology", 2nd ed., vol. II, pp. 396–402.

Primary Examiner—Joseph E. Evans
Attorney, Agent, or Firm—Shea & Gould

[57] ABSTRACT

Process for producing olefin oxides by means of the reaction of an olefin with oxygen or air, in the presence of a catalyst constituted by titanium silicalite and a redox system comprising alkyl-anthrahydroquinone and alkyl-anthraquinone, with said reaction being carried out in a solvent mixture consisting of:

(a) one or more aromatic or alkyl-aromatic, mono- or polynuclear hydrocarbon(s) selected from among benzene, toluene, xylene, alpha-methyl-naphthalene or halogenated derivatives thereof, such as dichlorobenzene;

(b) one or more polar organic compound(s) with boiling point comprised within the range of from 150° to 350° C., and selected from among di-isobutylcarbinol, di-isobutyl-ketone, methyl-cyclohexyl acetate, dimethyl phthalate, dibutyl phthalate, diethylhexyl phthalate and tert-butyl phthalate;

(c) a low molecular weight alcohol, preferably methanol.

19 Claims, 1 Drawing Sheet

PROCESS FOR PRODUCING OLEFIN OXIDES

The present invention relates to a process for producing olefin epoxides by starting from olefins and oxygen or air, in the presence of a catalyst constituted by a titanium silicalite and a redox system comprising alkyl-anthrahydroquinone and alkyl-anthraquinone.

From European patent 100,119, it is known that olefin oxides can be produced by means of the reaction of an olefin with hydrogen peroxide, or a compound capable of supplying hydrogen peroxide under reaction conditions, in the presence of a titanium silicalite.

The process disclosed in above-said patent makes it possible olefin oxides to be produced with high yield values and conversion rates, but when hydrogen peroxide is used as the reactant, said process results, at least at present, to be penalized by the high cost of hydrogen peroxide.

On the other hand, the use of hydrogen peroxide precursors, such as, e.g., isopropyl hydroperoxide—as envisaged in above said patent, and obtained by means of isopropanol oxidation—imposes burdensome separation processes for the separation of the byproducts resulting from the reaction of formation of hydrogen peroxide, as well as problems of subsequent use of said byproducts (in particular of acetone, when isopropyl hydroperoxide is used).

In general, the application of conventional processes for hydrogen peroxide production to the process of production of olefin epoxides according to European patent 100,119 is not feasible, because the conditions under which hydrogen peroxide production reaction takes place are not such as to enable a production of olefin oxides to be attained with satisfactory results from the viewpoints of yield values and reaction rate.

The present Applicant found now a process which makes it possible olefin oxides to be produced by means of the reaction of an olefin with oxygen or air, in the presence of a catalyst constituted by titanium silicalite and a redox system comprising alkyl-anthrahydroquinone and alkyl-anthraquinone, with said reaction being carried out in a solvent mixture.

The solvent mixture used in the process according to the present invention is constituted by:
(a) one or more aromatic or alkyl-aromatic, mono- or polynuclear hydrocarbon(s) selected from among benzene, toluene, xylene, alpha-methyl-naphthalene or halogenated derivatives thereof, such as dichlorobenzene;
(b) one or more polar organic compound(s) with boiling point comprised within the range of from 150° to 350° C., and selected from among di-isobutylcarbinol, di-isobutyl-ketone, methyl-cyclohexyl acetate, dimethyl phthalate, dibutyl phthalate, diethylhexyl phthalate and test-butyl phthalate;
(c) a low molecular weight alcohol, preferably methanol.

The ratios by weight of the components of the mixture may vary within wide ranges, and can advantageously be comprised within the following ranges of values: a/b=0.01-1.5; a/c=0.01-60; b/c=0.2-100.

The olefin compounds which can be used in the following invention preferably are olefin hydrocarbons containing from 2 to 18 carbon atoms in their molecule, as well as the halogenated derivatives of these hydrocarbons, and preferably, the olefin hydrocarbons containing from 3 to 6 carbon atoms in their molecule.

The exoxidation reaction can be carried out at a temperature comprised within the range of from 0° C. to 60° C.

The epoxidation reaction can be carried out under atmospheric pressure, or, preferably, under a pressure comprised within the range of from 1 to 20 abs.atm.

The redox system which can be used in the process according to the present invention is constituted by one or more pairs of alkyl derivatives of anthrahydroquinone and anthraquinone; in particular, the following pairs: 2-ethyl-anthraquinone/2-ethyl-anthrahydroquinone; 2-tert.-butyl-anthraquinone/2-tert.-butyl-anthrahydroquinone; 2-sec.-butyl-anthraquinone/2-sec.-butyl-anthrahydroquinone can be advantageously used.

The catalyst which can be used in the process according to the present invention is selected from among those which are generally known as titanium silicalities, falling within the scope of the following general formula:

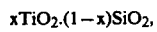

$$xTiO_2 \cdot (1-x)SiO_2,$$

with x comprised within the range of from 0.0001 to 0.04.

The above said titanium silicalites can be prepared according to the method as disclosed in U.S. Pat. No. 4,410,501, wherein also the structural characteristics of titanium silicalites are reported.

Also titanium silicalites can be used, in which a portion of titanium is replaced by other metals, such as aluminum, iron or gallium. These substituted titanium-silicalites, and the methods for producing them are disclosed in published European patent application Nos. 226,257; 226,258; and 266,825.

The oxidation reaction is preferably carried out in the presence of a smaller amount of alkyl-anthrahydroquinone than the stoichiometric amount advantageously, molar ratios of olefin to alkyl-anthrahydroquinone comprised within the range of from 1 to 5 will be used.

The amount of oxygen used—as pure oxygen, or as contained in air—will be such that the mixture of air or oxygen and olefin compound is out of the explosivity range and oxygen is in excess relatively to the required stoichiometric amount for the oxidation of alkyl-anthrahydroquinone. The preferred molar ratios of oxygen to alkyl-anthrahydroquinone are comprised within the range of from 1 to 1.5.

The invention is illustrated now by referring to FIG. 1, in which a schematic flow sheet of a preferred process for producing olefin epoxides is displayed.

To a reaction vessel (reactor) 1, equipped with a device, not shown in FIG. 1, to support the catalyst, the olefin compound is charged through line 2 and the solution of alkyl-anthrahydroquinone is charged through line 3. Oxygen or air are fed to the reactor 1 through line 4. Through the line 5, the reaction product is sent to a tower 6 in which the unreacted olefin compound, and the excess of oxygen are separated and are recycled, through line 2, to the reactor 1. If air is used, a venting off of an aliquot of recycle nitrogen must be provided for, after separating the olefin hydrocarbon.

The solution leaving from the bottom of the tower 6 is sent, through the line 7, to a separator 10; the organic phase is sent to the distillation tower 18, through the line 11; and the aqueous phase is sent to the distillation tower 13 through the line 12.

In the distillation tower 13 propylene oxide is separated as the overhead stream (effluent overhead stream 14), and water is removed through the line 15; the organic solution is sent, through the line 17, to the hydrogenation reactor 21, to which hydrogen is fed through the line 22. In the distillation tower 18 propylene oxide is separated as the overhead fraction, through the line 19, and the bottom product is sent to the hydrogenation reactor 21 through the line 20, which joins the line 17.

The following examples illustrate the invention in detail. Example 3 is supplied for comparative purposes.

EXAMPLE 1

To an autoclave of Pyrex glass, of 250 ml of capacity, 0.92 g of 2-ethyl-anthraquinone (3.9 mmol) dissolved in 30 ml of a solvent consisting of 2-methyl-naphthalene:-diisobutyl-ketone:methanol (22.5:67.5:10, by volume) and 0.10 g of 5% Pd/carbon are charged.

The autoclave is then charged with 3 bars of hydrogen. After 30 minutes of vigorous stirring at 20° C., the consumption of hydrogen (which corresponds to 0.43 bar) ceases. The suspension is filtered under an inert atmosphere, through a cellulose filter.

To a Pyrex-glass autoclave of 250 ml of capacity, 20 ml of solution of ethyl-anthrahydroquinone, obtained by means of the above operation, 0.052 g of titanium silicalite prepared according to Example 1 of U.S. Pat. No. 4,410,501 (0.31% by weight), and a known amount of methyl-tert.-butyl-ether (internal gaschromatographic standard) are charged. The autoclave is then charged with air and 3 bars of propylene, and the mixture is caused to react at 30° C., with strong stirring. At regular time intervals, samples of reaction mixture are drawn, and the amount of propylene oxide is determined by gaschromatography. After 31 minutes of reaction, the amount of propylene oxide corresponds to 50% of conversion of hydrogen peroxide theoretically formed by the reaction of reduction-oxidation of ethyl-anthraquinone/ethyl-anthrahydroquinone. The reaction comes to an end after 1 hour and 30 minutes, with a yield of 78% based on ethyl-anthrahydroquinone.

EXAMPLE 2

The process is carried out as in Example 1, but, instead of propylene, 3 bars of butene-1 is fed.

When reaction is complete, after 2 hours, 1,2-butene oxide is obtained with a yield of 70% based on charged anthraquinone.

EXAMPLE 3

The present example is supplied for comparison purposes and does not fall within the scope of the invention.

The test of Example 1 is repeated using a solvent mixture constituted by 2-methyl-naphthalene and diisobutyl-ketone (22:75 by volume), in the absence of methanol. After a 4-day reaction, propylene oxide is obtained with a yield of 23% based on used anthraquinone.

EXAMPLE 4

To an autoclave of Pyrex glass, of 250 ml of capacity, 1 g of 2-tert.-butyl-anthraquinone (3.8 mmol) and 0.7 g of 2-ethyl-anthraquinone (3 mmol) dissolved in 30 ml of a solvent based on di-isobutyl-carbinol:2-methylnaphthalene:methanol (50:40:10 by volume) and 0.270 g of 5% Pd/carbon are changed.

The autoclave is then charged with 4.6 bars of hydrogen. After that approximately 0.8 bar of hydrogen is consumed, the reaction is stopped and the resulting suspension is filtered under an inert atmosphere.

To a Pyrex-glass autoclave of 250 ml of capacity, 20 ml of the above said solution is charged together with 0.05 g of titanium silicalite (0.31% by weight) and 3 bars of propylene (about 28 mmol), 4-bar air and a known amount of methyl-tert.-butyl-ether (internal gas-chromatographic standard) are charged. The autoclave is immersed inside a thermostated bath at 30° C. After a 18-hour time, propylene oxide is obtained with a yield of 62.3% based on 2-tert.-butyl-anthraquinone.

We claim:

1. Process for producing olefin oxides by means of the reaction of an olefin with oxygen or air, in the presence of a catalyst constituted by a titanium silicalite and a redox system comprising alkyl-anthrahydroquinone and alkyl-anthraquinone, with said reaction being carried out in a solvent mixture constituted by:
   (a) one or more aromatic or alkyl-aromatic, mono- or polynuclear hydrocarbon(s) selected from among benzene, toluene, xylene, alpha-methyl-naphthalene or halogenated derivatives thereof,
   (b) one or more polar organic compound(s) with boiling point comprised within the range of from 150° to 350° C., and selected from among di-isobutylcarbinol, di-isobutyl-ketone, methyl-cyclohexyl acetate, dimethyl phthalate, dibutyl phthalate, diethylhexyl phthalate and tert-butyl phthalate; and
   (c) a low molecular weight alcohol.

2. Process for producing olefin oxides according to claim 1, characterized in that the starting olefin compounds are selected from among the olefin hydrocarbons containing from 2 to 18 carbon atoms in their molecule, or their monohalogenated derivatives.

3. Process for producing olefin oxides according to claim 2, characterized in that the starting olefin compounds are selected from among the olefin hydrocarbons containing from 3 to 6 carbon atoms in their molecule.

4. Process for producing olefin oxides according to claim 1, characterized in that the ratios by weight of the components of the mixture are selected from among the following values:
$a/b = 0.01-1.5$; $a/c = 0.01-60$; $b/c = 0.2-100$.

5. Process for producing olefin oxides according to claim 1, characterized in that the epoxidation reaction is carried out at a temperature comprised within the range of from 0° C. to 60° C.

6. Process for producing olefin oxides according to claim 1, characterized in that the epoxidation reaction is carried out under atmospheric pressure.

7. Process for producing olefin oxides according to claim 1, characterized in that the redox system is constituted by one or more pairs of alkyl derivatives of anthrahydroquinone and anthraquinone.

8. Process for producing olefin oxides according to claim 7, characterized in that the redox system is selected from among the following pairs: 2-ethyl-anthraquinone/2-ethyl-anthrahydroquinone; 2-tert.-butyl-anthraquinone/2-tert.-butyl-anthrahydroquinone; and 2-sec.-butyl-anthraquinone/2-sec.-butyl-anthrahydroquinone.

9. Process for producing olefin oxides according to claim 1, characterized in that the titanium silicalite used is selected from among those titanium silicalites, falling within the scope of the following general formula:

$$x\, TiO_2 \cdot (1-x) SiO_2,$$

with x comprised within the range of from 0.0001 to 0.04.

10. Process for producing olefin oxides according to claim 1, characterized in that in the titanium silicalite, used additionally contains another metal.

11. Process for producing olefin oxides according to claim 1, characterized in that the oxidation reaction is carried out with an amount of alkyl-anthrahydroquinone, less than the stoichiometric amount.

12. Process for producing olefin oxides according to claim 10, characterized in that the molar ratios of olefin to alkyl-anthrahydroquinone are comprised within the range of from 1 to 5.

13. Process for producing olefin oxides according to claim 1, characterized in that the amount of oxygen, as pure oxygen or as contained in air, will be such that the mixture of air or oxygen and olefin compound is out of the explosivity ranges and oxygen is in excess relative to the required stoichiometric amount for the oxidation of the alkyl-anthrahydroquinone.

14. Process for producing olefin oxides according to claim 1, characterized in that the molar ratios of oxygen to alkyl-anthrahydroquinone are comprised within the range of from 1 to 1.5.

15. Process for producing olefin oxides according to claim 1, characterized in that the reaction is carried out through the following steps:

to a reaction vessel 1 containing the catalyst, the olefin compound, the alkyl-anthrahydroquinone solution and oxygen or air are charged, the reaction product is sent to a tower 6 in which the unreacted olefin compound, and the excess of oxygen are separated and are recycled to the reactor 1, after possibly venting off an aliquot of recycle nitrogen, the solution leaving from the bottom of tower 6 is sent to a separation unit 10, the organic phase is sent to the distillation tower 18, and the aqueous phase is sent to the distillation tower 13, in the distillation tower 13 olefin oxide is separated as the overhead stream, and water is removed, and the organic solution is sent to a hydrogenation reactor 21, with, in the distillation tower 18 olefin oxide being separated as the overhead stream through the line 19, and the bottom product being sent to the hydrogenation reaction vessel 21, with the hydrogenated product being recycled to the oxidation reactor 1.

16. A process for producing olefin oxides according to claim 1, wherein, in part (a) the halogenated hydrocarbon derivatives is dichlorobenzene.

17. A process for producing olefin oxides according to claim 1, wherein the reaction is carried out under a pressure within the range of from 1 to 20 bars.

18. A process for producing olefin oxides according to claim 10, wherein the metal is selected from aluminum, iron and gallium.

19. A process producing olefin oxides according to claim 1, wherein, in part (c) the low molecular weight alcohol is methanol.

* * * * *